United States Patent [19]

Allan et al.

[11] Patent Number: 4,668,666

[45] Date of Patent: May 26, 1987

[54] LONG-ACTING PYRETHRUM/PYRETHROID BASED PESTICIDES WITH SILICONE STABILIZERS

[75] Inventors: G. Graham Allan, Seattle, Wash.; Thomas A. Miller, Satellite Beach, Fla.

[73] Assignee: Adams Veterinary Research Laboratories, Miami, Fla.

[21] Appl. No.: 678,404

[22] Filed: Dec. 5, 1984

[51] Int. Cl.$^4$ .................. A01N 55/00; A01N 65/00
[52] U.S. Cl. .................. 514/63; 514/974; 514/67
[58] Field of Search .................. 514/974, 67, 63

[56] References Cited

U.S. PATENT DOCUMENTS

| | | | |
|---|---|---|---|
| Re. 23,168 | 11/1949 | Smith et al. | 167/24 |
| 1,940,646 | 12/1933 | Grant | 514/919 |
| 1,963,955 | 6/1934 | Cleveland | 167/30 |
| 2,000,004 | 5/1935 | Adams | 167/39 |
| 2,011,428 | 8/1935 | Voorhees | 167/24 |
| 2,123,457 | 7/1938 | Wilson | 167/28 |
| 2,133,972 | 10/1938 | Coleman et al. | 167/24 |
| 2,144,368 | 1/1939 | Faloon | 167/24 |
| 2,151,651 | 3/1939 | Christmann et al. | 167/24 |
| 2,194,924 | 3/1940 | Coleman et al. | 167/24 |
| 2,203,919 | 6/1940 | Murphy | 167/22 |
| 2,421,223 | 11/1949 | Smith et al. | 167/24 |
| 2,772,198 | 11/1956 | Smith et al. | 167/24 |
| 3,093,536 | 6/1963 | Loeffler | 167/22 |
| 3,102,842 | 9/1963 | Phillips et al. | 167/30 |
| 3,560,613 | 2/1971 | Miskus et al. | 424/174 |
| 3,683,078 | 8/1972 | Haus | 424/190 |
| 3,852,416 | 12/1974 | Grubb et al. | 424/14 |
| 3,918,407 | 11/1975 | Greenberg | 119/156 |
| 3,944,662 | 3/1976 | Miller, Jr. et al. | 424/78 |
| 3,954,682 | 5/1976 | Fein et al. | 260/2.5 |
| 3,954,967 | 5/1976 | Urton | 424/81 |
| 4,134,977 | 1/1979 | Greenberg | 424/78 |
| 4,146,619 | 3/1979 | Lover et al. | 514/63 |
| 4,158,051 | 6/1979 | Greenberg et al. | 424/28 |
| 4,172,904 | 10/1979 | Young et al. | 427/4 |
| 4,190,680 | 2/1980 | Young et al. | 427/4 |
| 4,198,441 | 4/1980 | Young et al. | 427/2 |
| 4,200,664 | 4/1980 | Young et al. | 427/4 |
| 4,205,096 | 5/1980 | Young et al. | 427/4 |
| 4,212,897 | 7/1980 | Young et al. | 427/2 |
| 4,282,207 | 8/1981 | Young et al. | 424/78 |
| 4,282,208 | 8/1981 | Young et al. | 424/78 |
| 4,283,387 | 8/1981 | Young et al. | 424/78 |
| 4,320,139 | 3/1982 | Takei et al. | 424/282 |
| 4,376,113 | 3/1983 | Suglia et al. | 424/34 |
| 4,397,859 | 8/1983 | Geering | 514/67 |

FOREIGN PATENT DOCUMENTS 829556  3/1960  United Kingdom .................. 514/67

OTHER PUBLICATIONS

Miskus & Andrews, "Stabilization of Thin Films of Pyrethrins and Allethrin", J. Agr. Food Chem., vol. 20, No. 2, 1972, pp. 313-315.

Ong, "Chemistry & Uses of Insecticides", 1948, pp. 198-201.

*Primary Examiner*—Albert T. Meyers
*Assistant Examiner*—John M. Kilcoyne
*Attorney, Agent, or Firm*—Shapiro and Shapiro

[57] ABSTRACT

Pesticidal compositions based on nontoxic, naturally unstable insecticides (pyrethrum, synthetic pyrethroids and mixtures thereof) include a liquid alkyl aryl silicone polymer which stabilizes the insecticide to provide an extended effective killing life. The compositions additionally include a synergist to provide an immediate killing action and an antioxidant to protect the insecticide against destruction by oxygen. Ultraviolet protectants and insect repellents may also be included. Applications include control of insect pests to animals and plants and general purpose insect control. Exemplary formulations are given for compositions to be applied as sprays, dips, powdered or dusts, foggers and shampoos.

39 Claims, No Drawings

LONG-ACTING PYRETHRUM/PYRETHROID BASED PESTICIDES WITH SILICONE STABILIZERS

FIELD OF THE INVENTION

This invention relates to generally nontoxic, natural insecticides and synthetic derivatives made to mimic such insecticides. These natural insecticides (e.g., pyrethrum) are unstable in the environment and are characterized by a very short effective life. Their synthetic counterparts (e.g., the pyrethroids) exhibit similar characteristics, albeit to a lesser degree. The present invention is therefore concerned more particularly with improved pesticidal compositions, based on pyrethrum and/or synthetic pyrethroids, which achieve a significant prolongation of the effective killing life of the active insecticides through stabilization thereof.

BACKGROUND OF THE INVENTION

Biologically active agents for the control of ectoparasites and the like are a necessity of life and are particularly essential to the viability of commercial agriculture and to the welfare of the companion or pet animal community. In practice, these agents persist in their beneficial effects only so long as their active chemical structures can be maintained during exposure to hostile chemical environments (e.g., oxygen and ultraviolet sunlight). Chemical degradation caused by environmental elements has long been a problem with respect to natural insecticides, and in particular pyrethrum, a long-known natural insecticide which is an extract of the chrysanthemum flower.

Pyrethrum is detoxified rapidly by mammalian enzyme systems and is known to be quite safe for application to domestic animals and to plants as well ($LD_{50}$ in rats in the range of 500–1,000 mg/kilogram—see Casida, J. E., "Pyrethrum, The Natural Insecticide," Academic Press, 1973). In addition, pyrethrum is not teratogenic, carcinogenic or mutagenic. These characteristics make pyrethrum a highly desirable agent for pest control in numerous applications.

A major disadvantage of pyrethrum is its instability in the environment. Degradation commences immediately upon extraction from its natural source, the chrysanthemum flower, and proceeds at a substantially increased rate after application to a substrate to be treated, such as the coat of an animal, the surface of a plant, household surfaces, etc. The result is a very short effective life (several hours) which precludes pyrethrum as a practical alternative for general long-term pest control. Also, while the synthetic pyrethroids generally exhibit improved stability vis a vis pyrethrum, they too exhibit characteristic degradation—particularly after application in the environment (see Miskus and Andrews, infra, reporting stability on the order of about 4 hours for allethrin.)

In recent years, long-term pest control has generally involved the use of inherently more stable, synthesized insecticides (e.g., chlorinated hydrocarbons, carbamates and organophosphates) which are capable of maintaining sufficient efficacy in pest control for periods of days, or even weeks, after exposure to the environment. Notably, however, these insecticides are characterized by high mammalian toxicities and are frequently so toxic that they cannot be applied more than once in a 7–14 day time period. Indeed, many such insecticides are so toxic that they can never be safely applied for the control of ectoparasites on particularly sensitive companion animals such as cats.

Of particular concern in connection with companion animals is the fact that a major portion of the life cycles of ectoparasites generally does not take place on the host animal. Thus in order effectively to control such pests it becomes necessary to treat the animal's general living environment. Various longacting but toxic synthetic insecticides are frequently used for this purpose, including application indoors to carpeting, bedding and animal sleeping quarters as well as application outdoors to kennels, lawns, patios, etc. It has been observed that pet owners often make indiscriminate use of these synthesized insecticides, and this poses a substantial danger of toxicity to the animals intended to be protected as well as to the owners themselves. Moreover, the foregoing danger is frequently compounded by pet owner efforts to control other forms of pests by applying the same or similar toxic actives to the pet's general environment.

In view of such problems and with an increasing interest in safety and freedom from toxicity, significant efforts are currently being directed at replacing toxic synthesized insecticides with biodegradable pyrethrum and its synthetic counterparts (i.e., synthetic pyrethroids).

DESCRIPTION OF THE PRIOR ART

As early as the 1930's, there has been significant interest in extending the killing life of pyrethrum. Early efforts included the addition of antioxidants, such as hydroquinone, tannic acid and resorcinol, and ultraviolet absorbers to prevent pyrethrum degradation due to oxidation and exposure to sunlight. Despite these additions, the effective life of the insecticide was not extended appreciably. During World War II, when adequate amounts of pyrethrum were not available from Africa (its principal source), intensive work was undertaken to extend available pyrethrum stocks and utilize pyrethrum more effectively by incorporating synergists, which are today widely used with pyrethrum in controlling insect pests of man, his animals, and plants. The synergists act to augment the effect of pyrethrum. In particular, pyrethrum causes paralysis but not outright kill. Synergists, such as organic thiocyanates, may provide outright killing as a supplement to the pyrethrum paralytic action.

The six insecticidal constituents of pyrethrum extract are now identified and characterized by stereochemical configuration and the insecticidal activity of these fractions is better understood. The fractions are identified as pyrethrin I, cinerin I and jasmolin I, which represent the so-called chrysanthemate group, and pyrethrin II, cinerin II and jasmolin II, which represent the so-called pyrethrate group.

Pyrethrin I and cinerin I activities were studied intensively and reported by Miskus and Andrews in the article entitled, "Stablilization of Pyrethrins and Allethrin," published in the Journal of Agriculture and Food Chemistry, Vol. 20, No. 2, 1972 at Pages 313–315. Miskus and Andrews exposed pyrethrin I and cinerin I to sunlight for 4 hours in the presence of ultraviolet screening agents to study decomposition rates. Test formulations were prepared using different organic solvents including, inter alia, hexane, kerosene, and a selected commercial mineral oil. Mineral oil was the preferred solvent for stability, with better stability being obtained when antioxidants were also included in the preparations. Even with antioxidants present, however, the losses in strength of the pyrethrin and cinerin constituents were generally very substantial after exposure to sunlight for just 4 hours. Losses were particularly great in formulations prepared with kerosene, the vehicle in which pyrethrum is available commercially. Thus the literature exemplified by Miskus and Andrews assures a stability of pyrethrum only on the order of about 4 hours, with even less stability in the commercially available kerosene vehicle. Notably, in the same article, Miskus and Andrews reported about the same level of stability (4 hours) for allethrin (a synthetic pyrethroid), based on a similar series of experiments.

DISCOVERY OF THE INVENTION

The present invention, which achieves an effective killing life many times that previously attainable with pyrethrum-based insecticides, evolved out of the concept of a controlled release system through incorporation of pyrethrum into polymers. Initially, efforts were directed to the development of a pyrethrum-based spray including a low molecular weight polymer which would be present in a very small, but sufficient amount to inhibit the degradation of (i.e., to stabilize) the active insecticide in the environment. The inventors embarked upon a long series of experiments toward this end.

A first series of compositions was formulated with different molecular weight values of polyvinyl pyrrollidone as the intended polymer stabilizer, but these compositions demonstrated no prolonged insecticidal activity in comparison with control compositions containing no polymers. Thereafter, a number of other polymers, including polyvinyl acetate and polyethyl acrylate, were tried; but these compositions were found to be very difficult to apply to the coats of cats and dogs and far too sticky to be cosmetically acceptable. Thus no possibility for successful development of these compositions was apparent.

The next set of polymers examined by the inventors was polydimethylsiloxanes, which are available as nonvolatile, water-insoluble, low viscosity liquids. The objective was to achieve a controlled release delivery of the active insecticides while utilizing the beneficial cosmetic effect of liquid silicones. It was found, however, that all of the polydimethylsiloxanes tested (from very low to very high molecular weights) separated out into another phase when the diluent isopropanol evaporated. Therefore, a stable liquid polymeric residual composition could not be obtained after evaporation of the diluent.

Next, the inventors tested a low molecular weight alkyl aryl silicone—in particular, tetramethyltetraphenyltrisiloxane—although it was not considered likely to lead to success. Most of the silicones previously tested and reported in other controlled release systems are capable of forming high molecular weight materials by cross-linking both with themselves and with the animal hair substrate. Moreover, the high oxygen permeability of silicones would be expected to lead to more rapid degradation of pyrethrum. Surprisingly, however, it was found that the aforementioned siloxane polymer remained in homogeneous phase with the pyrethrum and other additives (antioxidant, ultraviolet absorbers, and repellents) and that the resulting residue upon evaporation of the isopropanol diluent provided a remarkably prolonged effective killing life in comparison with the control compositions. In particular, the killing life was extended to about 21 days—a vast improvement over the 4-hour period achieved in the prior art. Additionally, the siloxane polymer, due to its characteristically low viscosity, provided the desired cosmetic effect with ease of application; and the hydrophobic nature of the polymer provided a residue capable of remaining on the animal in spite of adverse environmental conditions such as rain. Later, other alkyl aryl silicones were examined and found to be similarly compatible stabilizers.

SUMMARY OF THE INVENTION

Generally stated, the invention resides in longacting pesticidal compositions for killing insects, comprising an insecticide selected from the group consisting of pyrethrum, synthetic pyrethroids and mixtures thereof, synergist for the insecticide in an amount effective to provide an immediate killing action, antioxidant in an amount effective to protect the insecticide against destruction by oxygen, and a water-insoluble silicone fluid which is essentially permanently liquid at 25° C. and which has a solvent action for the insecticide, synergist and antioxidant, the silicone fluid being present at a ratio to the active insecticide, in parts by weight, from about 1:10 to about 260:1.

Compositions according to the invention may also include one or more insect repellents in an effective amount to provide a residual insect repelling effect in addition to the prolonged insecticidal activity.

For compositions which are to be subject to exposure to light in the ultraviolet range after application, ultraviolet absorbers or screening agents which are soluble in the silicone polymer may be included in an effective amount to protect the active insecticide from destruction by such light.

Other aspects of the invention relate to the inclusion of various carrier or dispersant agents whereby the pesticidal compositions may be applied in liquid form (e.g., sprays, dips or shampoos), as a powder or dust, or as a fogger.

The invention provides numerous advantages in the control of insect pests. For example, as one of its advantages, the invention provides pesticidal compositions based on generally nontoxic, but naturally unstable insecticides (pyrethrum, synthetic pyrethroids and mixtures thereof) which achieve a greatly extended killing life over prior compositions based on the same insecticides.

As another advantage, the invention provides stabilized, nontoxic pesticidal compositions which form a long-lasting adherent coating on the treated substrate (e.g., the coat of an animal or the surface of a plant) that resists removal by adverse environmental conditions such as rain.

As still another advantage, the invention provides stabilized, nontoxic pesticidal compositions whereby the presence of a liquid alkyl aryl silicone stabilizer permits the use of very small amounts of active agents (insecticide, synergists, and repellents) while still providing long-term killing action, thereby permitting low-cost manufacture of the compositions.

Yet a further advantage of the invention is the provision of long-acting pesticidal compositions which are easy to apply to the coats of animals and which offer the cosmetic benefits of silicone.

The foregoing and other features and advantages of the invention will be more fully understood from the ensuing detailed description of the invention which includes exemplary pesticidal compositions for application as sprays, dips, dusts, shampoos and foggers.

DETAILED DESCRIPTION OF THE INVENTION

This section presents exemplary pesticidal compositions according to the invention. A first series of examples is given related to compositions which may be applied as sprays. Sprays for animals, plants and general use are included. A second series of examples relates to dips for application to animals by immersion or other suitable techniques such as sponging. A third series of examples relates to pesticidal dusts or powders for animals and plants. Finally, exemplary formulations are given for two total release foggers and for two animal shampoos.

Generally speaking, the compositions of the invention are characterized by the presence of an insecticide, a synergist for the insecticide to provide an outright killing effect, an antioxidant to protect the insecticide against destruction by oxygen, an alkyl aryl silicone polymer which is essentially permanently liquid at 25° C. and which has a solvent action for the aforementioned ingredients, and a carrier for applying all of the foregoing components. In addition to the components just identified, where it is desired to provide a residual insect repelling effect to inhibit reinfestation of the treated substrate, such as the coat of an animal, an insect repellent may also be included. Moreover, for compositions which will be exposed to ultraviolet light (e.g., those to be applied to outdoor plants or to animals which spend time outdoors), ultraviolet screening or absorbing agents may be included. It is to be understood that while the exemplary formulations presented hereinafter generally include repellents and/or ultraviolet screening agents, these components may be eliminated for those applications where such characteristics are deemed unnecessary.

The insecticides to which the invention applies include pyrethrum, synthetic pyrethroids and mixtures thereof. The usual commercial forms of pyrethrum and synthetic pyrethroids include the active insecticide in a petroleum distillate solvent (e.g., 20% w/w pyrethrum extract in kerosene, available under the trade designation Premium PYROCIDE 175 from the McLaughlin Gormley King Co., Minneapolis, Minn.). In practice, it may often be preferred, particularly for controlling ectoparasites on animals, to use pyrethrum alone or a mixture of pyrethrum with a synthetic pyrethroid since the former provides quick knock-down and flushing of pests, whereas the latter (the pyrethroids) generally work more slowly. A list of synthetic pyrethroids contemplated for use in practicing the invention appears following the specific examples to be given shortly. In the examples, the synthetic pyrethroids are referred to by common names, which may be crossreferenced with the chemical names using the aforementioned list.

Preferred synergists for practicing the invention include piperonyl butoxide and n-octyl-bicycloheptene dicarboximide. These synergists are available from the McLaughlin Gormley King Co., the latter being available under the trade designation MGK 264. Piperonyl butoxide has been widely used as a synergist in the industry, but has recently been discovered to be somewhat toxic to cats. MGK 264 does not have this effect and may advantageously be used along with or in place of piperonyl butoxide to reduce toxicity for applications to such sensitive animals. A list showing additional synergists which may be used to practice the invention appears after the specific examples.

The preferred antioxidant is butylatedhydroxytoluene (BHT). This material is readily available commercially and may be obtained, for example, from the Sherwin Williams Company. Other antioxidants are listed following the specific examples.

Preferred ultraviolet (UV) protectants include 2-ethylhexyl-p-dimethylaminobenzoate and 2-ethylhexyl-2-cyano-3,3'-diphenyl acrylate. The former is available under the trade designation ESCALOL 507 from Van Dyk & Company, Inc., Belleville, N.J.; and the latter is available under the trade designation UVINUL N-539 (or UVINUL 539) from the BASF Wayndotte Corporation, Parsippany, N.J. Another preferred UV absorber is p-amino benzoic acid (PABA). Additional UV protectants which may be useful in the practice of the invention are listed later.

Preferred repellents for use in practicing the invention include di-n-propyl isocinchomeronate (available under the trade designation MGK R326—McLaughlin Gormley King Company) and 2,3,4,5-bis(2-butylene)-tetrahydro-2-furaldehyde (available under the trade designation MGK R11—McLaughlin Gormley King Company). Additional repellents are listed following the specific examples.

Turning now to the silicone polymer component, preferred alkyl aryl silicones for implementing the invention are identified in Table I below. The identified silicones are pure liquids—all being solvents, nonvolatile, water-insoluble and based on polymers of phenylmethyl siloxanes. At 25° C. (the average temperature indoors for the environment of a domestic pet) all are essentially permanently liquid. The silicones are available commercially from the Dow Corning Corporation, Midland, Mich.

TABLE I

| PREFERRED SILICONES | |
|---|---|
| Trade Designation | Formula |
| DOW CORNING 550 | 50% phenyl, 50% dimethyl content in phenylmethylsilicone with linear backbone structure of siloxane, phenyl and methyl groups being on the side chains in equal molecular proportions; a single molecule product; molecular weight 750. |
| DOW CORNING 702 | Mixture of phenylmethylcyclosiloxane and dimethylcyclosiloxane. |
| DOW CORNING 704 | Tetramethyltetraphenyltrisiloxane; single molecule product; molecular weight 484. |
| DOW CORNING 705 | Pentaphenyltrimethyltrisiloxane; single molecule product; molecular weight 546. |
| DOW CORNING 710 | Phenylmethyltrisiloxane; 44% phenyl, 56% methyl content; single molecule product; molecular weight 2600. |

Table II below summarizes important typical properties of the above-identified silicones at 25° C. (77° F.). In addition to the properties specified in Table II, it is noted that the preferred silicones are further characterized by high thermal and chemical stability.

TABLE II

PROPERTIES OF PREFERRED SILICONES

| Trade Designation | Species | Vapor Pressure in Torr 25° C. | Viscosity, Centistokes 25° C. | Surface Tension at 25° C. Dynes/cm |
|---|---|---|---|---|
| DC 550 | Molecular Single Component | $3 \times 10^{-7}$ | 125 | 24.5 |
| DC 702 | Molecular Mixture | $1 \times 10^{-6}$ | 45 | 30 |
| DC 704 | Molecular Single Component | $2 \times 10^{-8}$ | 39 | 37.3 |
| DC 705 | Molecular Single Component | $3 \times 10^{-10}$ | 175 | 36.5 |
| DC 710 | Molecular Single Component | Too low to measure | 500 | 28.4 |

Referring now to the following Table III, the general parameters for compositions according to the invention are given. Specifically, Table III sets forth the approximate minimum and maximum ratios and the preferred range of ratios, in parts by weight, of silicone to insecticide for the compositions of the invention. The Table further specifies the preferred ranges for the content of synergists, antioxidants and ultraviolet protectants, all in terms of the insecticide-to-component ratio, in parts by weight. It will be appreciated by those skilled in the art that the amounts of these further components may be varied from the ranges given, but the specified ranges are preferred.

TABLE III

GENERAL FORMULATION PARAMETERS

| Components Ratio | Approx. Minimum | Preferred | Approx. Maximum |
|---|---|---|---|
| Silicone: Insecticide | 1:10 | 1:5–20:1 | 260:1 |
| Insecticide: Synergists | 1:50–1:5 | | |
| Insecticide: UV Protectants | 1:10–1:1 | | |
| Insecticide: Antioxidants | 1:10–1:1 | | |

The parameters appearing in Table III are applicable to each of the various forms of compositions discussed hereinafter (sprays, dips, dusts or powders, shampoos and foggers). In compositions for which a residual insect repelling effect is desired, one or more repellents such as those previously identified will also be included. An amount of repellent from about 0.25% to about 5% w/w of the final formulated product will generally be sufficient for this purpose; and while no particular ratio of insecticide-to-repellents is required, an approximate range of 1:4–1:20 may be used as a broad guideline in practice. In all cases an appropriate carrier will be added as a means for applying the remaining ingredients. For sprays, dips and shampoos, a volatile carrier is used—for dusts, a particulate carrier and for foggers, a propellant. The amount of alkyl aryl silicone liquid employed in each example is effective to wet the insecticidal ingredient used as well as any of the further components present.

Examples I–X relate to compositions for application as sprays. Table IV below shows exemplary general formulae for sprays on a percent weight basis. Formulae are given for each of the silicone-to-insecticide ratios in Table III.

TABLE IV

EXEMPLARY GENERAL SPRAY FORMULAE

| Components | % w/w (S/I Ratio 1:10) | % w/w (S/I Ratio 1:5) | % w/w (S/I Ratio 5:1) | % w/w (S/I Ratio 260:1) |
|---|---|---|---|---|
| Silicones | 0.025 | .05 | .25 | 5.20 |
| Insecticides | 0.25 | .25 | .05 | 0.02 |
| Synergists | 1.25 | 2.5 | 2.5 | 0.20 |
| Repellents | 0.5 | 1.0 | 1.0 | 0.40 |
| UV Protectants | 0.25 | .25 | .25 | 0.20 |
| Antioxidants | 0.25 | .25 | .13 | 0.20 |
| Volatile Carrier | 97.475 | 95.70 | 95.82 | 93.78 |

Spray formulations in accordance with Table IV above and as given in the specific examples may be prepared at room temperature according to the following procedure which is particularly suitable for preparing large quantities of product on the order of 2,000 gallons. The antioxidant is dissolved in a sufficient volume of a suitable solvent, usually volatile carrier, under agitation (for example, 1 part BHT in 10–20 parts isopropanol). With continued agitation, the insecticide is added to the preceding solution, followed by the addition of the synergists, UV protectants and insect repellents, and then the balance of the volatile carrier. The resulting preparation is then added slowly to the silicone liquid which is vigorously agitated to cause thorough mixing and uniform dispersion and thereby provide a homogeneous stable fluid product.

It should be noted that for aqueous emulsion systems (i.e., those with a mixed water/alcohol base with emulsifiers for phase stability), such as the formulations of Examples VII–IX, a slightly modified preparative procedure will be used. The initial steps are basicaly the same as those of the previous procedure. The antioxidant is dissolved in the alcohol carrier, and the insecticide, synergists, UV protectants and repellents are added to the resulting solution—all with agitation. This preparation is then added slowly to the silicone liquid with vigorous agitation. Upon completion of these initial steps, the emulsifiers are then added, with continued agitation. Finally, this preparation is added slowly to the water phase as the water phase is stirred.

EXAMPLE I

Illustrative Animal Spray No. 1

| Component | Function | Concentration % w/w |
|---|---|---|
| Pyrethrum | Insecticide | 0.10 |
| Piperonyl butoxide | Synergist | 0.37 |
| MGK 264 | Synergist | 0.61 |
| MGK R11 | Repellent | 0.20 |
| MGK R326 | Repellent | 0.20 |
| ESCALOL 507 | UV absorber | 0.25 |
| UVINUL 539 | UV absorber | 0.25 |
| BHT | Antioxidant | 0.20 |
| Silicone DC 704 | Polymer | 0.51 |
| Isopropanol | Volatile Carrier | 96.51 |
| Petroleum distillate (from pyrethrum concentrate) | | 0.40 |
| Fragrance, inerts | | 0.40 |

The following test procedure and results for the above formulation demonstrate the effectiveness of compositions according to the invention. For testing purposes, the above composition was placed and stored in an opaque plastic bottle composed of high-density polyethylene to which a trigger sprayer was attached to permit the generation of a mist or spray. The composition was then tested according to the following procedure.

Ten dogs, randomly divided into two groups of five, were exposed to infestation by fleas and ticks by placing on their coats newly emerged, unfed dog fleas (Ctenocephalides) and ticks (Rhipicephalus). One group of dogs was then treated with the formulation of this example, and the other group was left untreated to serve as a control. Each of the treated dogs was lightly misted over its entire body surface with a gloved hand being drawn across the coat in a direction opposite the lay of the hair. The average dose rate per animal weight was about 2.8 cc. per pound.

The hair coats of both groups were examined at various intervals by experienced examiners to determine the numbers of fleas and ticks surviving (without removal of or harm to the fleas and ticks). Both groups of dogs were repeatedly reinfested with new fleas and ticks and following reinfestation were examined repeatedly to determine establishment and survival of these new parasites. The following Table V shows the extended efficacy of the pesticidal composition against the identified parasites.

TABLE VI

| Time (Days) | Infest/ Treat | Average Numbers of Fleas and Ticks Surviving | | | |
|---|---|---|---|---|---|
| | | Ticks | | Fleas | |
| | | Treated | Control | Treated | Control |
| −1 | Infest | | | | |
| 0 | | 17.2 | 14.2 | 30.8 | 21.6 |
| | Treat | | | | |
| 3 (hrs.) | | 9.0 | 14.2 | 0 | 19.8 |
| 5 (hrs.) | | 3.0 | 13.2 | 0 | 19.6 |
| 1 | | 2.0 | 12.0 | 0 | 16.8 |
| 2 | | 0.2 | 11.2 | 0 | 15.2 |
| 5 | | 0.8 | 11.0 | 0 | 12.6 |
| | Reinfest | | | | |
| 6 | | 2.2 | 20.4 | 0 | 36.0 |
| 8 | | 1.2 | 19.8 | 0 | 35.0 |
| | Reinfest | | | | |
| 9 | | 2.8 | 21.0 | 0 | 33.4 |
| 12 | | 1.6 | 20.8 | 0 | 34.4 |
| | Reinfest | | | | |
| 13 | | 4.4 | 22.4 | 0.2 | 42.2 |
| 16 | 3.2 | 16.6 | 0.2 | 32.6 | |
| | Reinfest | | | | |
| 17 | | 6.8 | 28.8 | 2.0 | 49.0 |
| 21 | | 4.2 | 24.4 | 0 | 43.8 |
| | Reinfest | | | | |
| 22 | | 8.4 | 29.4 | 4.6 | 48.2 |

In another test, conducted for comparative purposes, a standard commercially available flea spray containing the active ingredients (i.e., insecticide, synergist and repellent) at higher levels but without the composition of this invention, namely the antioxidants, the UV light protectants and silicone polymer, was used to treat a group of dogs experimentally infested with fleas and ticks of the same species. The following Table VI shows that although this formulation produces immediate killing of the parasites, the killing action is very short-lived since successful reinfestation with fleas and ticks was accomplished in a very short time.

TABLE VI

| Time (Days) | Infest/ Treat | Average Numbers of Fleas and Ticks Surviving | | | |
|---|---|---|---|---|---|
| | | Ticks | | Fleas | |
| | | Treated | Control | Treated | Control |
| −1 | Infest | 27 | 37 | 114 | 95 |
| 0 | Treat | | | | |
| 1 | | 0 | 38 | 6 | 125 |
| 2 | | 0 | 42 | 7 | 108 |
| 5 | Reinfest | | | | |
| 6 | | 5 | 64 | 39 | 114 |
| 8 | Reinfest | | | | |
| 9 | | 91 | 63 | 150 | 156 |

EXAMPLE II

| Illustrative Animal Spray No. 2 | | |
|---|---|---|
| Component | Function | Concentration % w/w |
| Pyrethrum | Insecticide | 0.05 |
| Piperonyl butoxide | Synergist | 0.16 |
| MGK 264 | Synergist | 2.0 |
| MGK R11 | Repellent | 0.5 |
| MGK R326 | Repellent | 0.5 |
| ESCALOL 507 | UV absorber | 0.13 |
| UVINUL 539 | UV absorber | 0.13 |
| BHT | Antioxidant | 0.13 |
| Silicone DC 704 | Polymer | 0.25 |
| Isopropanol | Volatile Carrier | 95.55 |
| Petroleum distillate (from pyrethrum concentrate) | | 0.2 |
| Fragrance, inerts | | 0.4 |

The foregoing recipe illustrates another animal spray containing the ingredients of the composition of Example I, but at different concentrations. It is noted that while the sprays in both Examples I and II were formulated with the silicone polymer DC 704, any of the other preferred silicones could have been readily substituted therefor.

The formulation of this example was tested for efficacy concurrently with that of Example I, using a third group of five dogs and the same treatment, infestation and examination protocol as was previously described. Table VII shows that the present formulation achieved a level of extended efficacy which is substantially the same as that of the Example I formulation.

TABLE VII

| Time (Days) | Infest/ Treat | Average Numbers of Fleas and Ticks Surviving | | | |
|---|---|---|---|---|---|
| | | Ticks | | Fleas | |
| | | Treated | Control | Treated | Control |
| −1 | Infest | | | | |
| 0 | | 13.4 | 14.2 | 25.4 | 21.6 |
| | Treat | | | | |
| 3 (hrs.) | | 7.8 | 14.2 | 0.4 | 19.8 |
| 5 (hrs.) | | 2.2 | 13.2 | 0 | 19.6 |
| 1 | | 0.4 | 12.0 | 0 | 16.8 |
| 2 | | 0 | 11.2 | 0 | 15.2 |
| 5 | | 0.4 | 11.0 | 0 | 12.6 |
| | Reinfest | | | | |
| 6 | | 2.2 | 20.4 | 0 | 36.0 |
| 8 | | 1.2 | 19.8 | 0 | 35.0 |
| | Reinfest | | | | |
| 9 | | 1.6 | 21.0 | 0 | 33.4 |
| 12 | | 1.4 | 20.8 | 0 | 34.4 |
| | Reinfest | | | | |
| 13 | | 4.6 | 22.4 | 0.2 | 42.2 |
| 16 | | 2.0 | 16.6 | 0 | 32.6 |
| | Reinfest | | | | |

TABLE VII-continued

| Time (Days) | Infest/ Treat | Ticks Treated | Ticks Control | Fleas Treated | Fleas Control |
|---|---|---|---|---|---|
| 17 | | 5.2 | 28.8 | 0.4 | 49.0 |
| 21 | | 1.4 | 24.4 | 0 | 43.8 |
| | Reinfest | | | | |
| 22 | | 6.0 | 29.4 | 2.4 | 48.2 |

Average Numbers of Fleas and Ticks Surviving

EXAMPLE III

The following recipe represents three additional animal sprays respectively formulated with the silicones DC 550, 704 and 710.

Illustrative Animal Sprays Nos. 3-5

| Component | Function | Concentration % w/w |
|---|---|---|
| Pyrethrum | Insecticide | 0.10 |
| Piperonyl butoxide | Synergist | 0.37 |
| MGK 264 | Synergist | 0.61 |
| MGK R11 | Repellent | 0.20 |
| MGK R326 | Repellent | 0.20 |
| ESCALOL 507 | UV absorber | 0.25 |
| UVINUL 539 | UV absorber | 0.25 |
| BHT | Antioxidant | 0.20 |
| Silicone DC 550, 704 or 710 | Polymer | 0.25 |
| Isopropanol | Volatile Carrier | 96.77 |
| Petroleum distillate (from pyrethrum concentrate) | | 0.40 |
| Fragrance, inerts | | 0.40 |

The sprays represented by the above recipe were tested for comparative efficacy using the same basic procedure described in connection with Example I. Each spray was applied to a respective test group of four dogs (average dose rate 2.8 cc. per pound), with an additional group of four untreated dogs serving as a control. All dogs were infested repeatedly with fleas and ticks and were examined at intervals by non-destructive/non-removal techniques to determine flea and tick survival counts. Tables VIII and IX show the extended efficacy of these three sprays.

TABLE VIII

Group Flea Counts (F) and Treatment Efficacies $(E_f)$*

| Time After Treatment | Control F | Spray 3 (DC 550) F | Spray 3 $E_f$ | Spray 4 (DC 704) F | Spray 4 $E_f$ | Spray 5 (DC 710) F | Spray 5 $E_f$ |
|---|---|---|---|---|---|---|---|
| Pretreatment | 59 | 81 | — | 70 | — | 55 | — |
| 3 hours | 55 | 0 | 100 | 0 | 100 | 0 | 100 |
| 5 hours | 52 | 0 | 100 | 0 | 100 | 0 | 100 |
| 1 day | 47 | 0 | 100 | 0 | 100 | 0 | 100 |
| 2 | 50 | 0 | 100 | 0 | 100 | 0 | 100 |
| 5 | 38 | 0 | 100 | 0 | 100 | 0 | 100 |
| Reinfest | | | | | | | |
| 6 | 63 | 0 | 100 | 0 | 100 | 0 | 100 |
| 8 | 63 | 0 | 100 | 0 | 100 | 0 | 100 |
| Reinfest | | | | | | | |
| 9 | 75 | 0 | 100 | 4 | 94.7 | 3 | 96 |
| 12 | 66 | 0 | 100 | 3 | 95.5 | 1 | 98.5 |
| Reinfest | | | | | | | |
| 13 | 94 | 29 | 69.2 | 17 | 81.9 | 16 | 83 |
| 16 | 90 | 14 | 84.4 | 19 | 78.9 | 5 | 94.4 |
| Reinfest | | | | | | | |
| 17 | 118 | 30 | 74.6 | 43 | 63.6 | 22 | 81.4 |
| 21 | 114 | 16 | 86 | 39 | 65.8 | 13 | 88.6 |

*Efficacy in treated groups for first 5 days post-treatment measured by comparing flea burdens with respective group's pre-treatment burdens. After reinfestation on 5th day, efficacies measured by comparing treated with control flea burdens.

TABLE IX

Group Tick Counts (T) and Treatment Efficacies $(E_t)$*

| Time After Treatment | Control T | Spray 3 (DC 550) T | Spray 3 $E_t$ | Spray 4 (DC 704) T | Spray 4 $E_t$ | Spray 5 (DC 710) T | Spray 5 $E_t$ |
|---|---|---|---|---|---|---|---|
| Pretreatment | 80 | 70 | — | 103 | — | 65 | — |
| 3 hours | 77 | 12 | 82.9 | 17 | 83.5 | 16 | 75.4 |
| 5 hours | 75 | 8 | 88.6 | 6 | 94.2 | 6 | 91 |
| 1 day | 79 | 0 | 100 | 2 | 98.1 | 1 | 98.5 |
| 2 | 81 | 0 | 100 | 1 | 99 | 1 | 98.5 |
| 5 | 34 | 0 | 100 | 1 | 99 | 0 | 100 |
| Reinfest | | | | | | | |
| 6 | 108 | 1 | 99.1 | 3 | 97.2 | 4 | 96.3 |
| 8 | 95 | 0 | 100 | 0 | 100 | 0 | 100 |
| Reinfest | | | | | | | |
| 9 | 115 | 3 | 97.4 | 9 | 92.2 | 3 | 97.4 |
| 12 | 92 | 0 | 100 | 5 | 94.6 | 1 | 98.9 |
| Reinfest | | | | | | | |
| 13 | 121 | 12 | 90.1 | 18 | 85.1 | 12 | 90.1 |
| 16 | 122 | 2 | 98.4 | 18 | 85.2 | 6 | 95.1 |
| Reinfest | | | | | | | |
| 17 | 123 | 22 | 82.1 | 37 | 69.9 | 10 | 91.9 |
| 21 | 107 | 19 | 82.2 | 32 | 70.1 | 9 | 91.6 |

*Efficacy in treated groups for first 5 days post-treatment measured by comparing tick burdens with respective group's pre-treatment burdens. After reinfestation on 5th day, efficacies measured by comparing treated with control tick burdens.

EXAMPLE IV

The following formulation represents another animal spray in accordance with the invention, this particular spray being based on the synthetic pyrethroid permethrin together with synergized pyrethrum. This composition is formulated to be particularly useful as a residual fly repellent when sprayed or wiped onto the coat of equines. Thickening agents such as carboxymethyl cellulose, hydroxyethyl cellulose, gum acacia, or alginates or carageenan may be added to make a viscous adherent lotion.

Illustrative Animal Spray No. 6

| Component | Function | Concentration % w/w |
|---|---|---|
| Permethrin | Insecticide | 0.10 |
| Pyrethrum | Insecticide | 0.10 |
| Piperonyl Butoxide | Synergist | 0.50 |
| MGK R11 | Repellent | 0.20 |
| MGK R326 | Repellent | 0.20 |
| Butoxypropylene Glycol | Repellent | 1.50 |
| ESCALOL 507 | UV absorber | 0.25 |
| UVINUL 539 | UV absorber | 0.25 |
| BHT | Antioxidant | 0.20 |
| Silicone DC 704 | Polymer | 0.25 |
| Petroleum Distillate (from insecticide concentrates) | | 0.55 |
| Isopropanol | Volatile Carrier | 55.9 |
| Water | Volatile Carrier | 40.0 |

EXAMPLE V

This Example shows another animal spray in accordance with the invention. This particular spray is based on the synthetic pyrethroid deltamethrin together with synergized pyrethrum for an immediate knockdown and killing action. Notably, the very high insecticidal activity of deltamethrin (greater than 10 times the activity of permethrin) permits the use of a low insecticide concentration which, in turn, facilitates practice of the concept of the invention with only a very small concentration of silicone polymer being required. The formulation would provide immediate knockdown and kill and prolonged effective insecticidal life, with reduced cost due to the small amount of silicone polymer and insecticide necessary.

Illustrative Animal Spray No. 7

| Component | Function | Concentration % w/w |
| --- | --- | --- |
| Deltamethrin (100% Technical) | Insecticide | 0.01 |
| Pyrethrum | Insecticide | 0.05 |
| MGK 264 | Synergist | 0.30 |
| MGK R11 | Repellent | 0.25 |
| ESCALOL 507 | UV absorber | 0.10 |
| UVINUL 539 | UV absorber | 0.10 |
| BHT | Antioxidant | 0.06 |
| Silicone DC 705 | Polymer | 0.10 |
| Petroleum Distillate (from pyrethrum concentrate) | | 0.20 |
| Isopropanol | Volatile Carrier | 68.83 |
| Ethanol | Volatile Carrier | 30.0 |

The above spray is formulated to be particularly useful as a residual ectoparasiticide and repellent for dogs. For application to cats which are irritated by alcohol fumes, the isopropanol and ethanol may be replaced by water (except a sufficient amount to provide a volatile solvent during preparation), and a small quantity (e.g., 0.1%) of a cationic surfactant would be added to provide a stable emulsion. A surfactant having an HLB (hydrophilic lipophilic balance) value of about 13 would be suitable for this purpose. An exemplary surfactant would be CAT-13, available from Armak Company, Industrial Chemicals Division, Chicago, Ill.

EXAMPLE VI

The following formulations are for two additional animal sprays based on pyrethrum.

Illustrative Animal Spray No. 8

| Component | Function | Concentration % w/w |
| --- | --- | --- |
| Pyrethrum | Insecticide | 0.10 |
| Piperonyl butoxide | Synergist | 0.37 |
| MGK 264 | Synergist | 0.61 |
| MGK R11 | Repellent | 2.0 |
| MGK R326 | Repellent | 2.0 |
| ESCALOL 507 | UV absorber | 2.5 |
| UVINUL 539 | UV absorber | 2.5 |
| BHT | Antioxidant | 1.0 |
| Silicone DC 704 | Polymer | 26.0 |
| Isopropanol | Volatile Carrier | 61.52 |
| Petroleum distillate (from pyrethrum concentrate) | | 0.40 |
| Fragrance,inerts | | 1.0 |

Illustrative Animal Spray No.9

| Component | Function | Concentration % w/w |
| --- | --- | --- |
| Pyrethrum | Insecticide | .10 |
| Piperonyl butoxide | Synergist | .37 |
| MGK 264 | Synergist | .61 |
| MGK R11 | Repellent | 1.0 |
| MGK R326 | Repellent | 1.0 |
| ESCALOL 507 | UV absorber | 1.5 |
| UVINUL 539 | UV absorber | 1.5 |
| BHT | Antioxidant | 0.75 |
| Silicone DC 704 | Polymer | 14.0 |
| Isopropanol | Volatile Carrier | 78.17 |
| Petroleum distillate (from pyrethrum concentrate) | | 0.40 |
| Fragrance,inerts | | 0.6 |

EXAMPLE VII

The following is an exemplary formulation of a general purpose surface spray in accordance with the invention. The spray is based on the synthetic pyrethroid phenothrin.

Illustrative General Purpose Surface Spray No. 1

| Component | Function | Concentration % w/w |
| --- | --- | --- |
| Phenothrin | Insecticide | 1.536 |
| Related Compounds* | Insecticide | 0.064 |
| Piperonyl Butoxide | Synergist | 8.00 |
| p-amino benzoic acid | UV absorber | 6.00 |
| BHT | Antioxidant | 1.60 |
| Silicone DC 550 | Polymer | 0.32 |
| Petroleum Distillate (from phenothrin concentrate) | | 0.16 |
| Emulsifier (sulfonated petroleum oil-e.g., SPONTO 140T, Witco Chemical Co.) | | 5.00 |
| Isopropanol | Solvent/ Volatile Carrier | 15.00 |
| Water | Volatile Carrier | 62.32 |

*contained in commercial phenothrin concentrate, available from McLaughlin Gormley King; includes other isomers of 3-phenoxybenzyl d-cis and trans 2,2-dimethyl-3-(2-methylpropenyl) cyclopropanecarboxylate.

This spray is formulated, in concentrate form, to be useful when diluted 1 part with 32 parts of water (approximately 4 ounces per gallon) and applied at the rate of 1 gallon diluted spray per 1000 square feet of surface to be treated for controlling insects (e.g., fleas, ticks, cinch bugs, ants, chiggers, webworms, mole crickets, etc.) outdoors. Exemplary applications include vegetation, lawn, patio, kennels, porches, yards, verandas, and crawl spaces. For indoor use (e.g., to control fleas, ticks, cockroaches, etc.), the diluted spray would be sprayed at a rate of 1 gallon per 2000 square feet of surface—for example, on floors, into cupboards and closets, around baseboards, behind appliances, under furniture and on a pet's bed.

EXAMPLE VIII

This example provides another formulation for a general purpose spray. This spray is based on the synthetic pyrethroid d-trans allethrin and is formulated for application in diluted form as described in connection with the spray of the preceding example.

| Illustrative General Purpose Surface Spray No. 2 | | |
| --- | --- | --- |
| Component | Function | Concentration % w/w |
| d-trans allethrin | Insecticide | 0.32 |
| Related Compounds* | Insecticide | 0.02 |
| MGK 264 | Synergist | 3.40 |
| p-amino benzoic acid | UV absorber | 1.92 |
| BHT | Antioxidant | 1.60 |
| Silicone DC 710 | Polymer | 6.40 |
| Petroleum Distillate (from insecticide concentrate) | | 0.01 |
| Isooropanol | Solvent/ Volatile Carrier | 16.00 |
| CAT 13 | Emulsifier | 1.00 |
| Water | Volatile Carrier | 69.33 |

*Contained in commercial d-trans allethrin concentrate, available from McLaughlin Gormley King; includes other isomers of 2-allyl-4-hydroxy-3-methyl-2-cyclopent-en-1 ester of 2,2-dimethyl-3-2(2-methylpropenyl)-cyclopropanecarboxylic acid.

EXAMPLE IX

This Example shows the formulaton for an agricultural spray based on the synthetic pyrethroid tetramethrin for application to growing crops. The formula shown is for a concentrate which would preferably be diluted with water at one quart per 100 gallons of water and applied at a rate of 100 gallons of diluted spray per acre.

| Illustrative Spray for Growing Crops | | |
| --- | --- | --- |
| Component | Function | Concentration % w/w |
| Tetramethrin | Insecticide | 4.00 |
| Related compounds* | Insecticide | 0.54 |
| Piperonyl Butoxide | Synergist | 10.00 |
| MGK 264 | Synergist | 10.00 |
| p-amino benzoic acid | UV absorber | 4.54 |
| BHT | Antioxidant | 4.54 |
| Silicone DC 710 | Polymer | 4.54 |
| Isopropanol | Solvent/ Volatile Carrier | 20.00 |
| Petroleum Distillate (from Tetramethrin concentrate) | | 0.4 |
| Emulsifier (e.g., TRITON X-100**, Rohm and Haas Co.) | | 5.0 |
| Water | Volatile Carrier | 36.44 |

*contained in commercial tetramethrin concentrate, available from McLaughlin Gormley King
**octylphenoxypolyethoxyethanol Examples X and XI show illustrative emulsion dips for application to animals. Basically, the emulsions of the invention involve an alkyl aromatic silicone maintained in water by the use of an appropriate emulsifier. The particular emulsifier selected in practice will depend upon the characteristics of the silicone polymer used. The emulsifier may be selected by testing the stability of silicone-water blends at various HLB values using a typical HLB test kit. Generally, a cationic surfactant with an HLB value from about 13 to about 15 will provide good results (e.g., CAT-13 discussed in Example IV, CAT-15, available from the same source, and mixtures of these). It is noted that there is no fundamental difference between a liquid formulation and an emulsion formulation. When the water in an emulsion evaporates the equivalent of a liquid formulation will be left behind. The emulsions of Examples X and XI can be prepared according to the modified procedure described in connection with the preparation of sprays.

EXAMPLE X

This Example shows a pyrethrum-based dip for animals in accordance with the invention.

| Illustrative Animal Dip No. 1 | | |
| --- | --- | --- |
| Component | Function | Concentration % w/w |
| Pyrethrum | Insecticide | 1.0 |
| Piperonyl Butoxide | Synergist | 4.0 |
| MGK 264 | Synergist | 6.0 |
| MGK R326 | Repellent | 2.0 |
| MGK R11 | Repellent | 2.0 |
| ESCALOL 507 | UV absorber | 1.0 |
| Univul 539 | UV absorber | 1.0 |
| BHT | Antioxidant | 1.0 |
| Silicone DC 705 | Polymer | 20.0 |
| Petroleum Distillate (from Pyrethrin) | | 4.0 |
| Isopropanol | Solvent/ Volatile Carrier | 10.0 |
| Emulsifier (e.g., CAT 13 +/or CAT 15) | Emulsifier | 0.5 |
| Water | Volatile Carrier | 47.5 |

This dip is formulated for application (after dilution at the rate of 1 oz. per gallon of water) to dogs and cats by immersion or sponging to control, inter alia, fleas, tick and lice. It could also be used as a spray for cattle and horses to provide immediate and residual control of ticks, biting flies and other pests. Diluted at the rate of 1 pint per 100 gallons of water per acre, this product could also be sprayed onto plants (agricultural and horticultural) for control of chewing and sucking insect pests such as caterpillars, beatle larvae, plant bugs and aphids. For such applications the repellents may, of course, be eliminated.

EXAMPLE XI

This Example shows another emulsion formulation according to the invention. The formulation is based on the synthetic pyrethroid permethrin together with pyrethrum and is shown as a concentrate which may be diluted at a rate of 0.5 oz. to 1 gallon of water for use.

| Illustrative Dip for Animals No. 2 | | |
| --- | --- | --- |
| Component | % w/w Concentrate | Concentration % w/w, when diluted 0.5 oz. per gallon H2O for use |
| Permethrin | .79 | 0.0031 |
| Pyrethrum | 1.35 | 0.0053 |
| Piperonyl Butoxide | 5.04 | 0.0197 |
| MGK 264 | 8.13 | 0.0318 |
| MGK R11 | 2.71 | 0.0106 |
| MGK R326 | 2.71 | 0.0106 |
| ESCALOL 507 | 3.39 | 0.0132 |
| UVINUL 539 | 3.39 | 0.0132 |
| Component | Concentration % w/w (Concentrate) | Concentration % w/w, when diluted 0.5 oz. per gallon for use |
| BHT | 2.71 | 0.0106 |
| Silicones    DC 550 | 9.85 | 0.0385 |
|                    DC 704 | 9.85 | 0.0385 |
| CAT 13 | 0.63 | 0.0025 |
| CAT 15 | 0.16 | 0.0006 |
| Isopropanol | 27.10 | 0.1059 |

| Illustrative Dip for Animals No. 2 | | |
|---|---|---|
| Water | 16.59 | 99.674 |
| Petroleum Distillate (from permethrin and pyrethrin concentrates). | 5.60 | 0.0219 |

Examples XII through XVI show exemplary dust formulations in accordance with the invention. The liquid portion of the dusts may be compounded as a concentrate using the procedure described in connection with sprays under Example I and then coated on a suitable dispersant such as silica gel (e.g., SYLOID 244 available from the W. R. Grace Co.). Coating may be accomplished, for example, by spraying the liquid concentrate on the dispersant (carrier) dust under agitation followed by drying of the dust with forced air or in a low temperature oven. Upon evaporation of the isopropanol or other volatile solvent during drying, a residue comprising a solution of actives in the siloxane fluid would remain on the silica gel. Thereafter, calcium carbonate or another inert filler may be added to expand the dust to a suitable and economic concentration for use. The following Table X shows illustrative general formulations for preparing dust compositions according to the invention at the approximate minimum and maximum silicone-to-insecticide ratios shown previously at Table III herein. The corresponding formulations for the dried dusts prepared according to Table X appear in Table XI.

TABLE X

| Exemplary General Dust Formulations (Preparative) | | |
|---|---|---|
| | Minimum S:I % w/w | Maximum S:I % w/w |
| Phenylmethyl Siloxane | 0.02 | 5.2 |
| Pyrethrum/Pyrethroid | 0.2 | 0.02 |
| Ratio S:I | 1:10 | 260:1 |
| Synergists | 1.0 | 0.2 |
| Repellents | 0.8 | 0.2 |
| UV Protectants | 0.2 | 0.2 |
| Antioxidants | 0.2 | 0.2 |
| Solvents | 10.0 | 10.0 |
| Carrier (e.g., silica gel | 10.0 | 10.0 |
| Petroleum Distillate | 0.8 | 0.08 |
| Calcium Carbonate, Talc, etc. | 76.78 | 73.9 |

TABLE XI

| Exemplary General Dust Formulations (Dry) | | |
|---|---|---|
| | Minimum S:I % w/w | Maximum S:I % w/w |
| Phenylmethyl Siloxane | 0.0225 | 5.7829 |
| Pyrethrum/Pyrethroid | 0.2247 | 0.0222 |
| Ratio S:I | 1:10 | 260:1 |
| Synergists | 1.1237 | 0.2224 |
| Repellents | 0.8989 | 0.2224 |
| UV Protectants | 0.2247 | 0.2224 |
| Antioxidants | 0.2247 | 0.2224 |
| Carrier (e.g., silica gel | 11.2359 | 11.1210 |
| Calcium Carbonate, Talc, etc. | 86.0449 | 82.1843 |

EXAMPLE XII

The following formulation is for a pyrethrum-based dust for applicationn to animals.

| Illustrative Dust No. 1 | | | |
|---|---|---|---|
| Component | Function | Concentration (Preparative) % w/w | Concentration (Dry) % w/w |
| Pyrethrum | Insecticide | 0.182 | 0.2085 |
| Piperonyl Butoxide | Synergist | 0.57 | 0.6531 |
| MGK 264 | Synergist | 1.36 | 1.5584 |
| MGK R11 | Repellent | 0.45 | 0.5156 |
| MGK R326 | Repellent | 0.45 | 0.5156 |
| ESCALOL 507 | UV absorber | 0.45 | 0.5156 |
| UVINUL 539 | UV absorber | 0.45 | 0.5156 |
| BHT | Antioxidant | 0.45 | 0.5156 |
| Silicone DC 550 | Polymer | 2.00 | 2.2917 |
| Petroleum Distillate (from pyrethrum concentrate) | | 0.728 | — |
| Isopropanol | Volatile Solvent | 12.00 | — |
| Silica Gel | Dust Carrier | 10.0 | 11.4586 |
| Calcium Carbonate (100 mesh) | Filler | 70.91 | 81.2517 |

This dust or powder is formulated to be particularly useful for application to dogs and cats to control ticks. It could also be used to fill dust bags which can be suspended in cattle yards and pastures. Livestock rubbing against the bags would become coated with the dust which would provide insecticidal and repellent actions against, for example, biting flies.

EXAMPLE XIII

This Example shows a further pyrethrum-based dust formulation.

| Illustrative Dust No. 2 | | | |
|---|---|---|---|
| Component | Function | Concentration (Preparative) % w/w | Concentration (dry) % w/w |
| Pyrethrum | Insecticide | 1.0 | 1.042 |
| Piperonyl Butoxide | Synergist | 3.0 | 3.125 |
| MGK 264 | Synergist | 6.0 | 6.250 |
| MGK R11 | Repellent | 0.5 | 0.521 |
| MGK R326 | Repellent | 0.5 | 0.521 |
| ESCALOL 507 | UV absorber | 1.0 | 1.042 |
| UVINUL 539 | UV absorber | 1.0 | 1.042 |
| BHT | Antioxidant | 1.0 | 1.042 |
| Silicone DC 710 | Polymer | 2.5 | 2.604 |
| Petroleum distillate (from pyrethrum concentrate) | | 4.0 | — |
| Isopropanol | Volatile Solvent | 10.0 | — |
| Silica Gel | Carrier | 10.0 | 10.416 |
| Diatomaceous earth (e.q., talc) | Filler | 59.5 | 72.395 |

EXAMPLE XIV

The following formulation is for another dust for application to animals, particularly dogs and cats. The dust is based on the synthetic pyrethroids tetramethrin and phenothrin.

Illustrative Dust No. 3

| Component | Function | Concentration (Preparative) % w/w | Concentration (Dry) % w/w |
|---|---|---|---|
| Tetramethrin | Insecticide | 0.2 | 0.25 |
| Phenothrin | Insecticide | 0.12 | 0.15 |
| Related Compounds* | Insecticide | 0.005 | 0.006 |
| MGK 264 | Synergist | 3.25 | 4.064 |
| MGK R11 | Repellent | 0.5 | 0.625 |
| ESCALOL 507 | UV absorber | 0.163 | 0.204 |
| UVINUL 539 | UV absorber | 0.163 | 0.204 |
| BHT | Antioxidant | 1.625 | 2.032 |
| Silicone DC 702 | Polymer | 0.325 | 0.406 |
| Isopropanol | Volatile Solvent | 20.0 | — |
| Petroleum distillate (from insecticide concentrates) | | 0.033 | — |
| Silica Gel | Carrier | 12.0 | 15.007 |
| Diatomaceous Earth | Filler | 61.616 | 77.052 |

*contained in commercial pyrethroid concentrates, as noted earlier

EXAMPLE XV

This Example shows a dust formulation for growing crops based on the synthetic pyrethroid cypermethrin together with pyrethrum.

Illustrative Dust No. 4

| Component | Function | Concentration (Preparative) % w/w | Concentration (Dry) % w/w |
|---|---|---|---|
| Cypermethrin (technical 100%) | Insecticide | 0.05 | 0.053 |
| Pyrethrum | Insecticide | 0.10 | 0.106 |
| Piperonyl Butoxide | Synergist | 0.50 | 0.529 |
| p-amino benzoic acid | UV absorber | 1.50 | 1.585 |
| BHT | Antioxidant | 1.50 | 1.585 |
| Silicone DC 550 | Polymer | 3.00 | 3.172 |
| Petroleum Distillate (from pyrethrum concentrate) | | 0.40 | |
| Isopropanol | Volatile Solvent | 5.00 | |
| Talc, calcium carbonate or similar particulate | Carrier | 87.95 | 92.97 |

The above dust could be readily applied by a conventional fertilizer spreader or by aerial application (at a rate of 100 lb. per acre). The dust could also be granulated by replacing part of the carrier with a hydrophilic binder and then be applied by low-volume granular fertilizer spreading equipment, or mixed with granular fertilizer and spread therewith, to achieve control, inter alia, of top soil and soil surface dwelling phytophagous insect pests (e.g., cutworms, wireworms and the like).

EXAMPLE XVI

The following formulation shows a dust based on pyrethrum together with the synthetic pyrethroid d-trans allethrin. The particular dust below is formulated for application to companion animals for the control of fleas and ticks.

Illustrative Dust No. 5

| Component | Function | Concentration (Preparative) % w/w | Concentration (Dry) % w/w |
|---|---|---|---|
| d-trans allethrin | Insecticide | 0.93 | 0.983 |
| Related compounds* | Insecticide | 0.07 | 0.074 |
| Pyrethrum | Insecticide | 0.10 | 0.106 |
| Piperonyl Butoxide | Synergist | 0.50 | 0.529 |
| MGK 264 | Synergist | 0.50 | 0.529 |
| MGK R11 | Repellent | 0.20 | 0.211 |
| MGK R326 | Repellent | 0.20 | 0.211 |
| ESCALOL 507 | UV absorber | 0.10 | 0.106 |
| UVINUL 539 | UV absorber | 0.10 | 0.106 |
| BHT | Antioxidant | 0.20 | 0.211 |
| Silicone DC 550 | Polymer | 1.10 | 1.163 |
| Petroleum Distillate (from insecticide concentrates) | | 0.41 | — |
| Isopropanol | Volatile Solvent | 5.0 | — |
| Silica Gel | Carrier | 10.0 | 10.572 |
| Talc (100 mesh) | Filler | 80.59 | 85.199 |

*Contained in commercial pyrethroid concentrate, as noted earlier.

The final Examples XVII through XX show two illustrative environmental foggers and two illustrative animal shampoos in accordance with the invention.

EXAMPLE XVII

This Example shows a total release fogger based on pyrethrum. The fogger is formulated for release at a rate of 1.5 ounces per 5,000 cubic feet to be treated. It should be noted that foggers may be prepared by mixing the antioxidants, insecticides, synergists, UV absorbers and silicone as previously described in regard to sprays and then placed in a pressurized container with the propellant by conventional techniques.

Illustrative Fogger No. 1

| Component | Function | Concentration % w/w | gms. per 1.5 oz. fogger |
|---|---|---|---|
| Pyrethrum | Insecticide | 2.0 | 4.26 |
| Piperonyl Butoxide | Synergist | 4.0 | 1.74 |
| MGK 264 | Synergist | 6.0 | 2.55 |
| BHT | Antioxidant | 2.0 | 0.84 |
| ESCALOL 507 | UV absorber | 1.0 | 0.42 |
| UVINUL 539 | UV absorber | 1.0 | 0.42 |
| Silicone DC 550 | Polymer | 2.5 | 1.07 |
| Isopropanol | Volatile Solvent | 10.0 | 4.25 |
| Petroleum Distillate (from pyrethrum concentrate) | | 8.0 | 3.40 |
| Carrier/propellant (FREON 22) | | 63.5 | 27.83 |

The following test results in Table XII show the effectiveness of the above formulation. For test purposes, the fogger was applied in five 720 square foot mobile home trailers which had been infested with fleas. The trailers were reinfested at intervals and flea counts were taken repeatedly. Five untreated trailers served as controls.

TABLE XII

Flea Counts (Average per Trailer) and Fogger Efficacy

| Time (Days) | | Flea Count Treated | Control | Efficacy (%) |
|---|---|---|---|---|
| 0 | Infest & Treat | | | |
| 1 | | 19.2 | 292.6 | 93.5 |
| 2 | | 9.0 | 125.6 | 92.8 |
| 3 | Count & Reinfest | 10.6 | 35.0 | 69.7 |
| 4 | | 133.0 | 278.4 | 52.2 |
| 7 | Count & Reinfest | 26.4 | 98.6 | 73.2 |
| 8 | | 200.4 | 286.2 | 30.0 |
| 9 | | 34.2 | 164.2 | 79.2 |

EXAMPLE XVIII

This example shows a fogger based on the synthetic pyrethroids d-trans allethrin and phenothrin. The fogger is formulated for release at the rate of six ounces per 5,000 cubic feet to be treated.

Illustrative Fogger No. 2

| Component | Function | Concentration % w/w | gms. per 6 oz. fogger |
|---|---|---|---|
| d-trans allethrin | Insecticide | 0.3 | 0.51 |
| Related Compounds* | Insecticide | 0.023 | 0.04 |
| Phenothrin | Insecticide | 0.191 | 0.32 |
| Related Compounds* | Insecticide | 0.009 | 0.02 |
| MGK 264 | Synergist | 5.230 | 8.89 |
| p-amino benzoic acid | UV absorber | 2.092 | 3.56 |
| BHT | Antioxidant | 2.092 | 3.56 |
| Silicone DC 702 | Polymer | 0.052 | 0.09 |
| Petroleum Distillate (from insecticide concentrates) | | 0.029 | 0.05 |
| Methylene Chloride | Volatile Solvent | 10.0 | 17.01 |
| Trichlor-ethylene | Volatile Solvent | 10.0 | 17.01 |
| FREON 22 | Propellant/ Carrier | 69.982 | 119.04 |

*Contained in respective commercial pyrethroid concentrates, as noted earlier.

EXAMPLE XIX

This example shows an illustrative shampoo formulation in accordance with the invention. This particular shampoo is formulated for cleaning the coats of dogs and cats and for killing and repelling a variety of insect pests including, for example, fleas, ticks, mites, lice and mosquitoes. In practice, the formulations for shampoos would follow the same criteria and ratios for silicone and insecticide content as were explained previously for sprays, dips and dusts. The shampoo base and water for sudsing the shampoo act as the inert diluent in the same manner as the volatile carriers disclosed earlier in connection with sprays and dips. As with the previous applications of the invention, synthetic pyrethroids may be substituted for or mixed with pyrethrum.

The preparation of shampoos embodying the invention involves essentially the same steps described earlier as for preparing sprays. Briefly, the antioxidant is first dissolved in the volatile solvent, followed by the addition of the insecticides, synergists, repellents, UV absorbers and silicone, all with agitation. The shampoo base is prepared separately as a concentrate (for dilution by water) by standard mixing and agitation steps which are well known. The concentrated preparation of insecticidal actives and additives is added slowly to the shampoo base concentrate with continuous stirring. Additional water is then added, providing the balance of the shampoo base. Squeezable opaque, high density polyethylene containers with an air-tight sealable spout may be used to store and dispense the final product.

Illustrative Shampoo No.1

| Component | Function | Concentration % w/w |
|---|---|---|
| Pyrethrum | Insecticide | 0.15 |
| Piperonyl butoxide | Synergist | 1.50 |
| MGK 264 | Synergist | 0.50 |
| MGK R11 | Repellent | 0.50 |
| p-amino benzoic acid | UV absorber | 1.50 |
| BHT | Antioxidant | 1.50 |
| Silicone DC 550 | Polymer | 0.75 |
| Isopropanol | Volatile Solvent | 10.00 |
| Petroleum Distillate (from pyrethrum concentrate) | | 0.60 |
| Inert shampoo base* | Carrier | 83.0 |

*Conventional shampoo base containing deionized water, sodium lauryl sulfate, tea lauryl sulfate, propylene glycol USP, ethylene glycol monstearate, polyoxyethylene glycol, Lanolin, cocamide dea, Quaternarium 19, EDTA (ethylenediaminetetracetic acid), preservatives and FD & C Blue No. 1 color.

EXAMPLE XX

This final example shows an additional shampoo formulation in accordance with the invention. This shampoo is based on the synthetic pyrethroids d-trans allethrin and permethrin.

| Component | Function | Concentration % w/w |
|---|---|---|
| d-trans allethrin | Insecticide | 0.093 |
| Related Compounds* | Insecticide | 0.007 |
| Permethrin | Insecticide | 0.15 |
| MGK 264 | Synergist | 1.50 |
| MGK R326 | Repellent | 0.50 |
| ESCALOL 507 | UV absorber | 0.20 |
| UVINUL 539 | UV absorber | 0.20 |
| BHT | Antioxidant | 0.50 |
| Silicone DC 702 | Polymer | 5.0 |
| Petroleum Distillate (from insecticide concentrates) | | 0.34 |
| Isopropanol | Volatile Solvent | 10.0 |
| Inert Shampoo base (see Example XVIII) | Carrier | 81.51 |

*Contained in commercial d-trans allethrin concentrate, as noted earlier.

All of the foregoing Examples illustrate the concept of silicone liquid polymers employed in minimal amounts to enhance the effective killing life of the active insecticidal ingredients (pyrethrum, synthetic pyrethroids and mixtures thereof). The silicones are essentially non-volatile alkyl aryl silicones which range in volatility at room temperature from the phenyl methyl polysiloxane fluid exemplified by DC 550 up to the extremely non-volatile DC 710, the latter having a vapor pressure too low to measure at 250° C. The alkyl aryl silicones of the invention are preferably molecular species having high solvent power per se (e.g., DC 550, 702, 704, 705, 710 and mixtures of these). Mixtures of the preferred silicones can be varied to adjust the phenyl content. It will be noted that in many of the examples a silicone has been used which includes at least as many phenyl groups as methyl groups (e.g., DC 550). Obviously, the low vapor pressure of the preferred silicones can provide a residual liquid having a vapor pressure which is millions of times less than the conventional non-volatile ingredients of the disclosure (e.g., dimethylphthalate which has a vapor pressure in the range of 0.1–2 mmHg and serves as an insect repellent).

In addition, the invention may be practiced with halogenated alkyl aryl silicones in liquid form, these being known (e.g., chlorophenylmethyl silicone oil or even higher alkyl aryl silicones such as ethyl, propyl or butylphenyl silicones). The selection of these silicones involves greater expense; and for this reason they are not preferred, but it is within the spirit of the invention to employ these substances in the same molecular weight range and for the same purposes as described in connection with the examples.

Finally, there are other silicones which may be utilized in accordance with the invention, such as mixed polymers and copolymers made by reacting a mixture of alkyl chlorosilanes and phenyl chlorosilanes, these copolymers having a varying phenyl content depending upon the molar proportions of the phenyl chlorosilane starting material. It must be recognized that the silicone liquids of the type described herein are made available by the manufacturer and there are more than one manufacturer in the United States, for example, Dow Corning and General Electric Company, and these may also be obtained from numerous manufacturers in Europe and Japan. Some of these manufacturers supply the mixed polymer or copolymer having a varying phenyl content; for example, a silicone fluid is described at Page 525 in the Encyclopedia of Plastics Technology as having a content of 25 mol % of methylphenyl groups and another liquid is described as having a content of 15 mol % of chlorophenyl groups. These liquids are contemplated for use in the invention and their volatility would be of the order of DC 550, although the solvent power, because of the reduced phenyl content, would not be as great as the solvent power of DC 550 for the active ingredients.

Following now are the earlier referred to lists showing additional synthetic pyrethroids, synergists, antioxidants, repellents, ultraviolet protectants and volatile carriers which may be desirable for use in the practice of the invention. These lists are illustrative only and are in no way intended to limit the practice of the invention to the particular ingredients indicated, the scope of the invention being defined in the appended claims.

ILLUSTRATIVE SYNTHETIC PYRETHROIDS (with common industrial names)

2-allyl-4-hydroxy-3-methyl-2-cyclopenten-1 ester of 2,2-dimethyl-3-(2-methylpropenyl)cyclopropanecarboxylic acid (d-trans allethrin)

2,4-dimethylbenzyl-2,2-dimethyl-3-(2-methylpentyl)cyclopropanecarboxylate (Dimethrin)

1-cyclohexane-1,2-dicarboximidomethyl-2,2-dimethyl-3-(2-methylpropenyl)-cyclopropanecarboxylate (Tetramethrin)

3-phenoxybenzyl-d-cis-trans chrysanthemate (Phenothrin)

5-(phenylmethyl)-3-furanylmethyl-2,2-dimethyl-3-(2-methyl-1-propenyl)cyclopropanecarboxylate (Resmethrin) cyano-(3-phenoxyphenyl)methyl-4-chloro-alpha(1-methylethylbenzene acetate (Fenvalerate)

3-phenoxyphenylmethyl-(+)-cis-trans-3-(2,2-dichloroethenyl)-2,2-dimethylcyclopropanecarboxylate (Permethrin)

(+)-cyano-(3-phenoxyphenyl)methyl(+)-cis-trans 3-(2,2-dichloroethenyl)-2,2-dimethylcyclopropanecarboxylate (Cypermethrin)

alpha-cyano-3-phenoxybenzyl-d,cis-disbromochrysanthemate (Deltamethrin)

cyano(4-fluoro-3-phenoxyphenyl)methyl-3-(2,2-dichloroethenyl)-2,2-dimethyl cyclopropanecarboxylate

ILLUSTRATIVE SYNERGISTS TO ENHANCE NEURO TOXICITY

Piperonyl butoxide

N-octyl-bicycloheptane dicarboximide organic thiocyanates in which the organic group is a long aliphatic organic radical having between 8 and 14 carbon atoms such as octyl thiocyanate, nonyl thiocyanate, decyl thiocyanate and undecenyl thiocyanate octachlorodipropyl ether

ILLUSTRATIVE REPELLENTS 2,3,4,5-bis(2- butylene)tetrahydro-2-furaldehyde
butoxypolypropyleneglycol
N,N-diethyltoluamide
2-hydroxyethyl-n-octyl sulfide
dimethyl phthalate
di-n-propyl isocinchomeronate

ILLUSTRATIVE ANTIOXIDANTS butylated hydroxytoluene (BHT)
tert-butylhydroquinone (TBHQ)
butylated hydroxyanisole (BHA)
Ethoxyquin
ascorbic acid
inorganic salts of ascorbic acid
ascorbic palmitate
inorganic salts of propionic acid (e.g., propyl gallate, thiodipropionic acid, dilauryl thiodipropionate)

ILLUSTRATIVE ULTRAVIOLET LIGHT ABSORBERS octyldimethyl-aminobenzoate
2-ethylhexyl-2-cyano-3,3'-diphenyl acrylate
2-ethylhexyl-p-dimethylaminobenzoate
2,2'-dihydroxy-4,4'-dimethoxy-5,5-disulfobenzophenone
2-hydroxy-4-methoxy-benzophenone-5-sulfonic acid
2,2',4,4'-tetrahydroxybenzophenone phenyl salicylate 2-(2H-benzotriazol-2-yl)-p-cresol
2-ethoxyethyl-p-methoxycinnmate
p-amino-benzoic acid (PABA)

ILLUSTRATIVE VOLATILE SOLVENTS

Isopropanol, ethanol, acetone, isobutyl alcohol, methanol, methylethyl ketone, methylene chloride

The invention claimed is:

1. An insecticidal composition consisting essentially of an insecticidally effective amount of an insecticide selected from the group consisting of pyrethrum, synthetic pyrethroids and mixtures thereof, synergist for said insecticide in an amount effective to provide an enhanced killing action, antioxidant in an amount effective to protect said insecticide against destruction by oxygen, and non-volatile, water insoluble phenylmethylsiloxane polymer liquid which is a solvent for all of the aforesaid ingredients, said polymer liquid being present at a ratio to said insecticide, in parts by weight, from about 1:10 to about 260:1 and being effective to stabilize said insecticide.

2. A composition in accordance with claim 1, wherein said polymer liquids contains a phenylmethylsiloxane having at least as many phenyl groups as methyl groups.

3. A composition in accordance with claim 1, wherein said polymer liquid contains a linear phenylmethylsiloxane polymer having 50% phenyl groups and 50% dimethyl groups, with the phenyl and methyl groups being on the side chains in equal molecular proportions.

4. A composition in accordance with claim 3, wherein said linear phenylmethylsiloxane polymer has a molecular weight of about 750.

5. A composition in accordance with claim 1, wherein said polymer liquid contains phenylmethyltrisiloxane.

6. A composition in accordance with claim 5, wherein said phenylmethyltrisiloxane has about 44% phenyl groups and about 56% methyl groups and a molecular weight of about 2,600.

7. A composition in accordance with claim 1, wherein said polymer liquid contains a mixture of phenylmethylcyclosiloxane and dimethylcyclosiloxane.

8. A composition in accordance with claim 1, wherein said polymer liquids contains tetramethyltetraphenyltrisiloxane.

9. A composition in accordance with claim 1, wherein said polymer liquid contains pentaphenyltrimethylsiloxane.

10. A composition in accordance with claim 1, wherein said synergist is selected from the group consisting of piperonyl butoxide, n-octylbicycloheptene dicarboximide and mixtures thereof.

11. A composition in accordance with claim 1, wherein the ratio of insecticide to synergist, in parts by weight, is from about 1:50 to about 1:5.

12. A composition in accordance with claim 1, wherein said antioxidant includes butylatedhydroxytoluene.

13. A composition in accordance with claim 1, wherein the ratio of insecticide to antioxidant, in parts by weight, is from about 1:10 to about 1:1.

14. A composition in accordance with claim 1, wherein said polymer liquid is present at a ratio to said insecticide, in parts by weight, from about 1:5 to about 20:1.

15. A composition in accordance with claim 1, and a carrier for the foregoing components.

16. A composition in accordance with claim 15, wherein said carrier is a carrier selected from the group consisting of volatile solvents, dusts propellants, and inert shampoo bases.

17. A composition in accordance with claim 16, wherein said carrier is selected from the group consisting of the volatile solvents isopropanol, ethanol, and aqueous emulsions.

18. A composition in accordance with claim 16, wherein said carrier is silica gel dust.

19. An insecticidal composition consisting essentially of an insecticidally effective amount of an insecticide selected from the group consisting of pyrethrum, synthetic pyrethroids and mixtures thereof; synergist for said insecticide in an amount effective to provide an enhanced killing action; antioxidant in an amount effective to protect said insecticide against destruction by oxygen; at least one of ultraviolet protectant in an amount effective to protect said insecticide against destruction by ultraviolet light and insect repellent in an amount sufficient to provide an insect repelling effect; and non-volatile, water insoluble phenylmethylsiloxane polymer liquid which is a solvent for all of the aforesaid ingredients, said polymer liquid being present at a ratio to said insecticide, in parts by weight, from about 1:10 to about 260:1 and being effective to stabilize said insecticide.

20. A composition in accordance with claim 19, wherein each one of said synergist, said antioxidant, and said ultraviolet protectant present in said composition has the corresponding one of the following ratios of insecticide thereto, in parts by weight:

insecticide: synergist—from about 1:50 to about 1:5
insecticide:antioxidant—from about 1:10 to about 1:1
insecticide:ultraviolet protectant—from about 1:10 to about 1:1.

21. A composition in accordance with claim 20, wherein when said insect repellent is present, the ratio of insecticide to said repellent, in parts by weight, is from about 1:4 to about 1:20.

22. A composition in accordance with claim 20, wherein when said insect repellent is present, it is present in an amount from about 0.25% to about 5% by weight of said composition.

23. A composition in accordance with claim 19, wherein said polymer liquid contains a phenylmethylsiloxane having at least as many phenyl groups as methyl groups.

24. A composition in accordance with claim 19, wherein said polymer liquid contains a linear phenylmethylsiloxane having 50% phenyl groups and 50% dimethyl groups, with the phenyl and methyl groups being on the side chains in equal molecular proportions.

25. A composition in accordance with claim 24, wherein said linear phenylmethylsiloxane polymer has a molecular weight of about 750.

26. A composition in accordance with claim 19, wherein said polymer liquid contains phenylmethyltrisiloxane.

27. A composition in accordance with claim 26, wherein said phenylmethyltrisiloxane has a molecular weight of about 2,600 and contains about 44% phenyl groups and about 56% methyl groups.

28. A composition in accordance with claim 19, wherein said polymer liquid contains a mixture of phenylmethylcyclosiloxane and dimethylcyclosiloxane.

29. A composition in accordance with claim 19, wherein said polymer liquid contains tetramethyltetraphenyltrisiloxane.

30. A composition in accordance with claim 19, wherein said polymer liquid contains pentaphenyltrimethyltrisiloxane.

31. A composition in accordance with claim 19, wherein said ultraviolet protectant is selected from the group consisting of p-amino benzoic acid; 2-ethylhexyl-p-dimethylaminobenzoate; 2-ethylhexyl-2-cyano-3,3'-diphenyl acrylate and mixtures thereof.

32. A composition in accordance with claim 19, wherein said antioxidant contains butylatedhydroxytoluene.

33. A composition in accordance with claim 19, wherein said synergist is selected from the group consisting of piperonyl butoxide, n-octylbicycloheptene dicarboximide and mixtures thereof.

34. A composition in accordance with claim 19, wherein said polymer liquid is present at a ratio to said insecticide, in parts by weight, from about 1:5 to about 20:1.

35. A composition in accordance with claim 19, wherein said repellent is selected from the group consisting of di-n-propyl isocinchomeronate; 2,3,4,5-bis(2-butylene)-tetrahydro-2-furaldehyde and mixtures thereof.

36. A composition in accordance with claim 19, and a carrier for the foregoing components.

37. A composition in accordance with claim 36, wherein said carrier is a carrier selected from the group consisting of volatile solvents, dusts, propellants, and inert shampoo bases.

38. A composition in accordance with claim 37, wherein said carrier is selected from the group consisting of the volatile solvents isopropanol, ethanol, aqueous emulsions, and mixtures thereof.

39. A composition in accordance with claim 37, wherein said carrier is silica gel dust.

* * * * *